United States Patent
Subramanian

(10) Patent No.: US 8,390,806 B1
(45) Date of Patent: Mar. 5, 2013

(54) MEMS SPECTROMETER AND SENSING SYSTEMS THEREFROM

(75) Inventor: Suresh Subramanian, Ocoee, FL (US)

(73) Assignee: Lockheed Martin Corporation, Bethesda, MD (US)

( * ) Notice: Subject to any disclaimer, the term of this patent is extended or adjusted under 35 U.S.C. 154(b) by 251 days.

(21) Appl. No.: 12/785,218

(22) Filed: May 21, 2010

Related U.S. Application Data

(60) Provisional application No. 61/180,244, filed on May 21, 2009.

(51) Int. Cl.
  *G01J 3/28* (2006.01)
  *G01J 3/44* (2006.01)

(52) U.S. Cl. .......................... 356/328; 356/301

(58) Field of Classification Search ........... 356/300–334
See application file for complete search history.

(56) References Cited

U.S. PATENT DOCUMENTS

| | | | |
|---|---|---|---|
| 6,303,934 B1 * | 10/2001 | Daly et al. ............... | 250/339.02 |
| 6,657,723 B2 * | 12/2003 | Cohen et al. ............. | 356/328 |
| 6,862,092 B1 * | 3/2005 | Ibsen et al. .............. | 356/328 |
| 6,985,226 B2 | 1/2006 | Lerner | |
| 7,023,545 B2 * | 4/2006 | Slater .................... | 356/326 |
| 7,041,979 B2 * | 5/2006 | Chrisp ................... | 250/339.07 |
| 7,330,258 B2 * | 2/2008 | Warren .................. | 356/328 |
| 7,817,274 B2 * | 10/2010 | Zhang ................... | 356/328 |
| 8,040,507 B2 * | 10/2011 | Shibayama ............. | 356/328 |
| 2007/0236697 A1 * | 10/2007 | Zribi et al. .............. | 356/454 |
| 2009/0262346 A1 * | 10/2009 | Egloff et al. ............. | 356/326 |

* cited by examiner

*Primary Examiner* — Kara E Geisel
*Assistant Examiner* — Dominic J Bologna
(74) *Attorney, Agent, or Firm* — Beusse Wolter Sanks Mora & Maire, P.A.

(57) ABSTRACT

A MEMS spectrometer includes an optical substrate having a first face and a second face. A first semiconductor substrate is attached to the first face and includes a slit for passing incident light to the optical substrate, at least one integrated reflective grating, and at least one integrated detector array. A second semiconductor substrate is attached to the second face of the optical substrate and includes at least a first integrated mirror and a second integrated mirror. The first integrated mirror is positioned to receive the incident light transmitted by the optical substrate and to provide reflected light, and the integrated reflective grating, second integrated mirror and integrated detector array are positioned so that they are optically coupled to one another by the optical substrate to process the reflected light.

17 Claims, 3 Drawing Sheets

MEMS SPECTROMETER AND SENSING SYSTEMS THEREFROM

CROSS REFERENCE TO RELATED APPLICATIONS

This application and the subject matter disclosed herein claims the benefit of Provisional Application Ser. No. 61/180,244 entitled "MEMS SPECTROMETER AND SENSING SYSTEMS THEREFROM", filed May 21, 2009, which is herein incorporated by reference in its entirety.

FIELD

Disclosed embodiments relate to spectrometers, and in particular to MEMS spectrometers and sensing systems therefrom.

BACKGROUND

Spectrometers are optical instruments for measuring the absorption of light by chemical or biological materials. Spectrometers typically generate a plot of absorption versus wavelength or frequency, and the patterns produced are used to identify the substance(s) present, and their internal structure. Spectrometers generally comprise a source of electromagnetic radiation generally referred to as a light source, a wavelength selector (monochromator), a sample, a detector, a signal processor, and a readout.

Most spectroscopic methods can be differentiated as being either atomic or molecular based on whether or not they apply to atoms or molecules. Along with that distinction, spectroscopic methods can be classified based on the nature of their interaction. Absorption spectroscopy uses the range of the electromagnetic spectra in which a substance absorbs. This includes atomic absorption spectroscopy and various molecular techniques, such as infrared spectroscopy and Raman spectroscopy, in that region and nuclear magnetic resonance (NMR) spectroscopy in the radio region. Emission spectroscopy uses the range of electromagnetic spectra in which a substance radiates (i.e. emits). The substance first must absorb energy. This energy can be from a variety of sources, which determines the name of the subsequent emission, such as luminescence. Molecular luminescence techniques include spectrofluorimetry.

Scattering spectroscopy measures the amount of light that a substance scatters at certain wavelengths, incident angles, and polarization angles. The scattering process is much faster than the absorption/emission process. One of the most useful applications of light scattering spectroscopy is Raman spectroscopy.

Raman spectra contain vibrational information about the molecular species, thus allowing them to be uniquely identified with a spectral "fingerprint" by probing the molecule's vibration modes. Thus, Raman spectroscopy has potential applications in uniquely identifying chemical and biological agents. Unfortunately, Raman signatures are generally extremely weak and hence generally require large, delicate, bench-top spectrometers, with cooled detectors in order to detect the low level Raman signals emanating from the samples. This has limited the scope of Raman spectroscopy to generally being a research tool rather than an end-user diagnostics tool.

Surface Enhanced Raman Scattering (SERS) has emerged as an alternative to the traditional Raman scattering studies for species identification. SERS uses local, surface field enhancement to amplify the Raman scattering signal by many orders of magnitude (e.g., up to 10 to 12 orders of magnitude) as compared to conventional Raman spectroscopy. In SERS, a molecule or material to be identified is positioned in close proximity to one or more metallic nanoparticles, such as gold or silver nanoparticles. Due to proximity to the metal nanoparticle(s), the molecule to be identified experiences a greater electric field resulting from a resonant surface plasmon excitation, and consequently this enhanced evanescent field created near the surface of the nanoparticle amplifies the Raman vibrational mode and thus the Raman signal emanating from the molecule to be identified.

SERS studies in the laboratory using traditional Raman spectrometers have shown the capability to uniquely identify chemical agents and biological pathogens at very low concentrations approaching single molecule levels. SERS has therefore become an attractive modality for chemical and biological agent identification, such as for identifying pathogens. However, in order for a SERS spectrometer to become a practical field tool, a compact, light, rugged, and high performance spectrometer is needed.

SUMMARY

Disclosed embodiments include compact MEMS spectrometers and sensing systems therefrom adapted for portability. The MEMS spectrometer comprises an optical substrate having a first face and a second face. A first semiconductor comprising substrate "chip" is attached to the first face and includes a slit for passing incident light to the optical substrate, at least one integrated reflective grating, and at least one integrated detector array. A second semiconductor comprising substrate "chip" is attached to the second face of the optical substrate and includes at least a first integrated mirror and a second integrated mirror. The first integrated mirror is positioned to receive the incident light transmitted by the optical substrate and to provide reflected light, and the integrated reflective grating, second integrated mirror and integrated detector array are positioned so that they are optically coupled to one another by the optical substrate to process the reflected light.

In a typical embodiment, the respective semiconductor comprising substrates are attached to the optical substrate so that the optical components (grating(s), mirrors and photodetector array) are facing inward toward the optical substrate.

DETAILED DESCRIPTION

Figure 1:
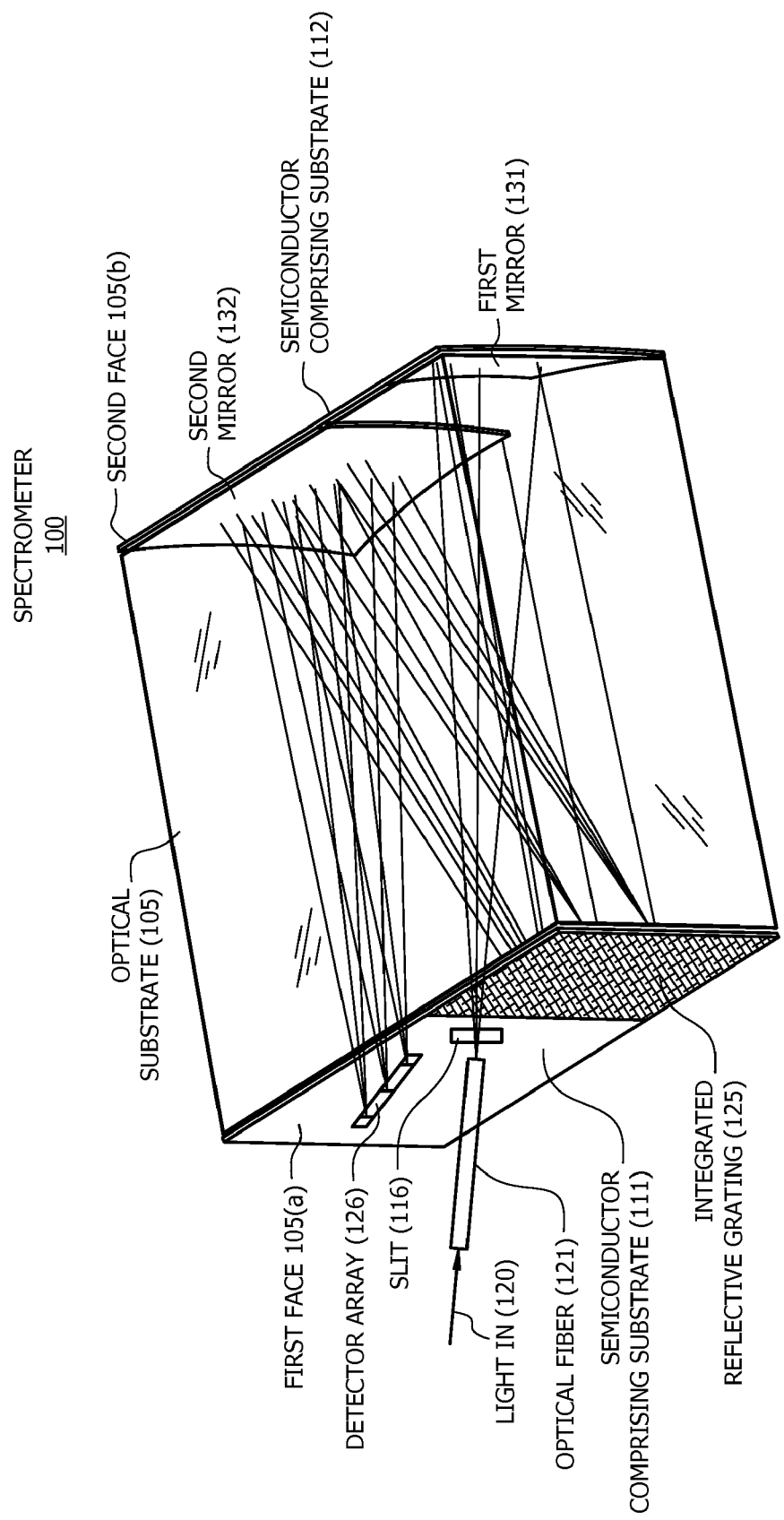
FIG. 1 is a depiction of a MEMS spectrometer including a raytrace shown, according to an embodiment of the invention.

Disclosed embodiments are described with reference to the attached figures, wherein like reference numerals, are used throughout the figures to designate similar or equivalent elements. The figures are not drawn to scale and they are provided merely to illustrate aspects disclosed herein. Several disclosed aspects are described below with reference to example applications for illustration. It should be understood that numerous specific details, relationships, and methods are set forth to provide a full understanding of the embodiments disclosed herein. One having ordinary skill in the relevant art, however, will readily recognize that the disclosed embodiments can be practiced without one or more of the specific details or with other methods. In other instances, well-known structures or operations are not shown in detail to avoid obscuring aspects disclosed herein. Disclosed embodiments are not limited by the illustrated ordering of acts or events, as some acts may occur in different orders and/or concurrently with other acts or events. Furthermore, not all illustrated acts or events are required to implement a methodology in accordance with this Disclosure.

Embodiments of the invention include high resolution, rugged, and compact spectrometers that are both small in size and lightweight for portability. Such spectrometers can be realized using MEMS/MOEMS and CMOS compatible designs fabricated using conventional semiconductor/MEMS manufacturing techniques (e.g., thin film deposition, lithography, ion implantation, and polishing/etching). Such spectrometers can deliver research grade spectroscopy capability in a practically maintenance free, pocket personal digital assistant (PDA) size package.

Although spectrometers are generally described herein for the SERS application, disclosed embodiments are generally applicable to a variety of other applications, and will generally be of particular benefit for rapid, portable, diagnostic sensing, such as for chemical and biological agent detection. Additional applications include, but are not limited to, infrastructure monitoring, chemical process monitoring, water purity monitoring. In each instance, the sample collection process will generally differ but the spectroscopic analysis tool (i.e. the MEMS spectrometer) remains the same. The MEMS spectrometer may be tuned to different resolutions and spectral wavelength windows using different detector types as appropriate to the application.

FIG. 1 is a depiction of a MEMS spectrometer 100 including a raytrace, according to an embodiment of the invention. MEMS spectrometer 100 includes an optical substrate 105 having a first face 105(*a*) and a second face 105(*b*). A first semiconductor comprising substrate "chip" (e.g., silicon, GaAs, or semiconductor on insulator (SOI)) 111 is attached (e.g. bonded) to the first face 105(*a*) of optical substrate 105 having a slit 116 for transmitting incident light 120 received via the optical fiber 121 shown to the first face 105(*a*) of the optical substrate 105. The tip of the optical fiber 121 can include a ball lens (not shown) fused to its tip for coupling light in or out of the slit 116 of the spectrometer 100. An integrated reflective grating 125 and at least one integrated photodetector array 126 having a plurality of detection pixels are both formed on the first semiconductor comprising substrate 111, typically both on a common semiconductor surface.

Integrated reflective grating 125 comprise a series of grooves to function as a wavelength dispersion element. As known in the art, the integrated reflective grating 125 can be generated by a ruling engine, replication, holographically, or by e-beam lithography. In one embodiment, the integrated reflective grating 125 can be a concave grating. Integrated reflective grating 125 can be a blazed grating. A blazed grating improves energy transfer of the grating to maximize efficiency at a specified wavelength. For example, a diffraction grating that is "blazed at 850 nm" will operate most efficiently when light with a wavelength of 850 nm is incident on the grating. Blazed gratings diffract incoming light using a series of grooves that are manufactured such that they form right angles with a specified "blaze angle," which is the angular distance from the surface normal of the diffraction plate. The magnitude of the blaze angle determines the wavelength at which the grating will be most efficient.

One consideration for typical applications for MEMS spectrometer 100 is stray light reaching the integrated detector array 126. The ray trace and faceting of components of the spectrometer 100 (e.g., first and second integrated mirrors 131 and 132 described below, etc.) are generally configured to ensure that stray light is rejected by the spectrometer 100 and thus is not detected since it does not reach the integrated detector array 126. In addition, as described below, unbonded faces of the optical substrate 105 can be covered or coated dark to prevent stray light from entering the spectrometer 100.

MEMS spectrometer 100 includes a second semiconductor comprising substrate ("chip") 112 having a semiconductor surface attached to the second face 105(*b*) of optical substrate 105 including a first integrated mirror 131 and at least a second integrated mirror 132 The integrated mirrors 131 and 132 can be plane or focusing (i.e., concave). The integrated mirrors 131 and 132 are both shown tilted, although this is not required. The first integrated mirror 131 reflects received incident light transmitted to it by the optical substrate 105 to provide reflected and optionally focused light that is directed to the integrated reflective grating 125. The second mirror 132 reflects and optionally also focuses light received from the integrated reflective grating 125 and directs this light to the integrated detector array 126 where it is detected.

The optical substrate 105 is generally selected from a low dispersion optical material for the optical range of interest, such as fused silica, $CaF_2$, ZnSe, $Al_2O_3$ (Sapphire), $MgF_2$, $BaF_2$ for operation from about 790 nm to 970 nm. The optical substrate 105 provides the spectrometer 100 improved mechanical rigidity since the substrates 111 and 112 are generally thin after fabrication or assembly thinning. For example, the thickness of the optical substrate 105 is generally at least 100 mils (about 2,540 μm), with a thickness of 1 inch (25.4 mm) being found to be possible based on some design work performed, and the thickness of the substrates 111 and 112 are generally <150 μm, typically 20 to 60 μms thick, such as obtained by conventional backgrinding the completed IC. In one embodiment the substrates 105, 111 and 112 generally have an area of roughly 0.5" (about 12.7 mm)× 3" (about 76.2 mm), or less. As noted above, the optical substrate 105 can also provide thermal stability due to a well-matched CTE between the optical substrate 105 and the substrates 111 and 112, particularly when the optical substrate 105 comprises silica and when the substrates 111 and 112 comprise silicon substrates.

The slit 116 can be formed using an etch process such as a conventional through silicon via (TSV) fab or assembly processing modified to exclude the metal (e.g., copper) filling Light is shown in the raytrace in FIG. 1 bouncing between integrated mirrors 131 and 132 and integrated grating 125 and getting dispersed by the integrated grating 125 onto the detector array 126 analogous to the raytrace for a traditional benchtop spectrometer.

The substrates 111 and 112 can be attached to the optical substrate 105 by an appropriate optical adhesive which can be selected to be optically clear and provide excellent light transmission properties for the wavelength range of interest. The substrates 111 and 112 can have fiducial markers and/or recesses in the respective corners that can function as precise receptacles for the substrates 111 and 112. Although not shown in FIG. 1, as noted above, the unbonded top and bottom, and front and back faces of the optical substrate 105 can be covered or coated dark to prevent stray light from entering the spectrometer 100.

Figure 2:
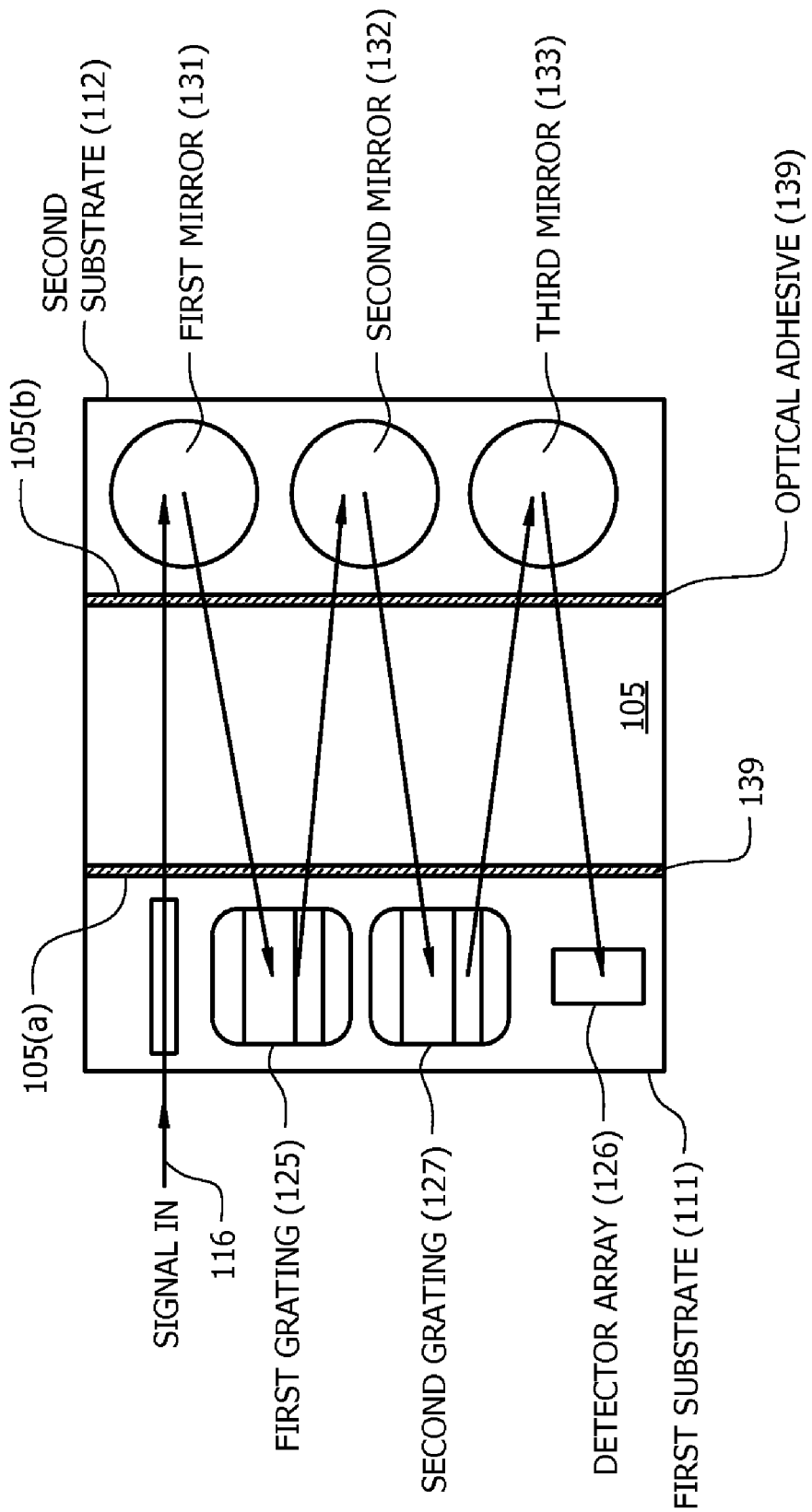
FIG. 2 is a depiction of a MEMS spectrometer including a directional raytrace shown, according to another embodiment of the invention.

FIG. 2 is a depiction of a MEMS spectrometer 150, according to another embodiment of the invention. MEMS spectrometer 150 adds a third integrated mirror 133 and a second integrated reflective grating 127 to the spectrometer components shown in FIG. 1. A layer of optical adhesive 139 is shown in FIG. 2. Adding additional mirrors and reflective gratings beyond that shown in FIG. 1, such as third integrated mirror 133 and second integrated grating 127 generally improves system performance, including its spectral resolution.

In operation of MEMS spectrometer 150, as shown in FIG. 2, light transmitted through the slit 116 to the substrate 105 propagates through the optical substrate 105 to integrated mirror 131 disposed on the surface of optical substrate 105 opposite the slit 116. The light is reflected onto an integrated reflective grating 125 residing alongside the slit 116. The integrated reflective grating 125 disperses this light onto integrated mirror 132 which reflects the light back to a second integrated grating 127. Integrated grating 127 in turn disperses and directs the light to integrated mirror 133 which finally projects a spectral image of the slit 116 onto 2D integral detector array 126.

The various components on the substrates 111 and 112 can all be fabricated using conventional MEMS processing, typically using a common side for the respective components. For example, integrated detector array 126, such as CMOS (i.e. photodiode, phototransistor or avalanche diode) detector array alongside the optics (e.g., integrated grating and optional integrated mirror) can be formed on substrate 111, with the integrated mirrors being formed on substrate 112, thus making all the functional components for spectrometers according to embodiments of the invention capable of being all MEMS & CMOS foundry built.

The spectrometer 100 shown in FIG. 1 represents an off-axis design, such as an Offner design, whereas the spectrometer 150 shown in FIG. 2 roughly follows that of a traditional Czerny Turner spectrometer (i.e., focusing-mirror/plane-grating, focusing-mirror/plane-grating, focusing-mirror/detector). Other embodiments such as toroidal or concave grating spectrometer that reduces the number of optical elements in the design. It is noted that a toroidal or concave grating can be diffractively etched onto a planar substrate, such as a planar silicon substrate. In each case, the spectrometers 100 and 150 have no discrete components since the respective spectrometer components including the detector array, reflective grating(s) and mirrors are integrated into one single monolithic block that comprises two semiconductor comprising substrates ("chips") bonded on respective sides of an optical substrate. The MEMS spectrometer is thus rugged as it is monolithic and has no moving parts. The MEMS spectrometer can also be largely athermal, particularly when the substrates 111 and 112 comprise bulk silicon and the optical substrate 105 comprises silica glass which are well thermally matched (i.e. close CTE matching), and thus will expand or contract together when heated or cooled. The only impact from heating above room temperature will generally be slight defocusing of light and resulting slight blurring. However, the spectrometer can be designed with a tight blur spot (relative to the detector pixel size), making this effect generally negligible.

A very low dispersion glass for the spectral bands of concern (e.g., 790 nm to 970 nm in the SERS application) is generally selected for optical substrate 105 to ensure minimal chromatic aberration. An alternative embodiment can use matching graded refractive index glass materials to form two compensating sections of substrate 105 that can be used to compensate for chromatic aberrations. It is also possible to deliberately introduce off axis errors like coma and astigmatism to compensate chromatic errors that cannot otherwise be corrected in all reflective designs.

Figure 3:
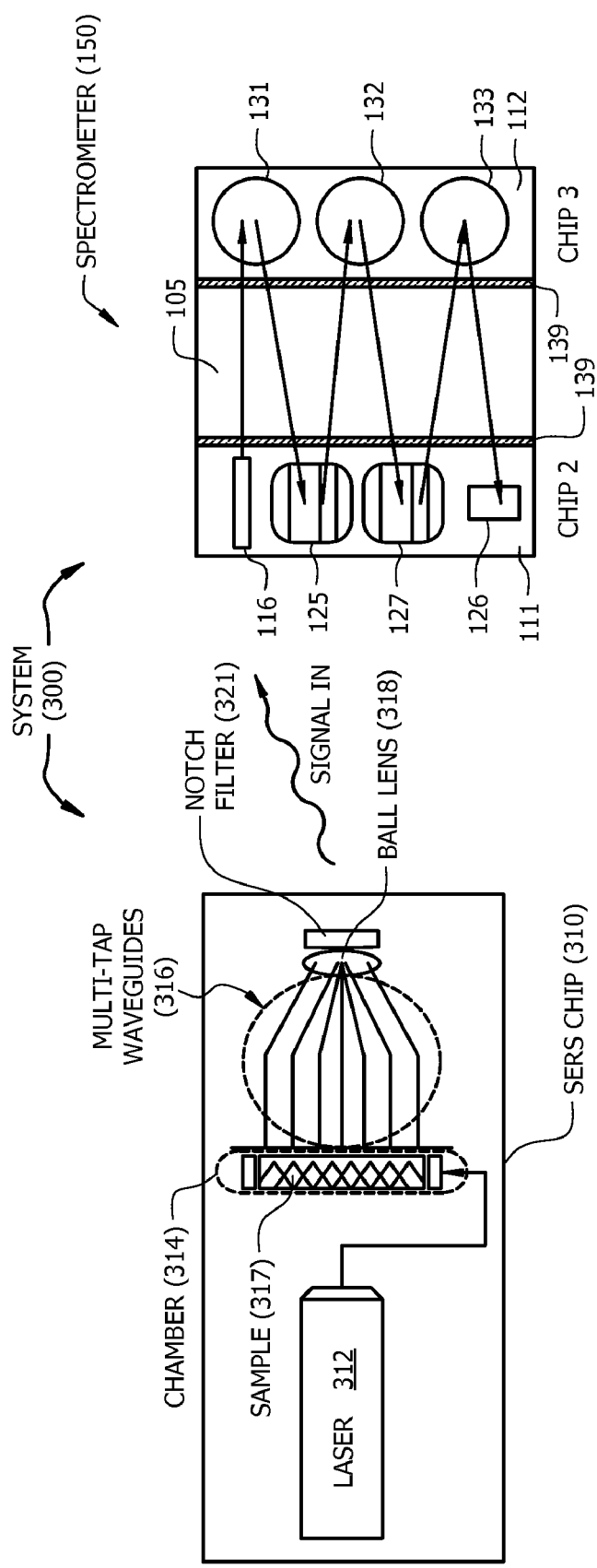
FIG. 3 is a depiction of a SERS sensing system comprising a SERS probe chip coupled to a MEMS spectrometer, according to an embodiment of the invention.

FIG. 3 is a depiction of a SERS sensing system 300 comprising the MEMS spectrometer 150 shown in FIG. 2 together with a SERS probe chip 310 comprising a light source 312, SERS reflective sample chamber 314 having reflective ends that can comprise a replaceable silicon nano-array having sample 317 thereon, and waveguide 316, according to an embodiment of the invention. Sample chamber 314 provides the sample collection area for system 300. Light source 312 can comprise various light sources including a laser or light emitting diode (LED), such as a microchip laser.

Waveguides 316 can comprise the multi-tap silicon waveguide shown for collecting light associated with the detection signal(s) emanating from the sample 317 or reporters (e.g., fluorescent tags) present in the sample 317. A ball lens 318 at end of waveguide 316 focuses the light into spectrometer 150. A laser notch filter 321 is provided for rejecting the elastically scattered radiation (parasitic Rayleigh signal) that can be attached the SERS probe chip 310 opposite to the SERS sample chamber 314.

In operation of system 300, light associated with the detection signal is collected that emanates from the sample 317 or reporters associated with the sample by a separate (e.g. silicon) waveguide 316 and is focused into the entrance slit 116 of the spectrometer 150 using a lens, such as the fast ball lens 318 shown optically bound to the end of the waveguide 316. Notch filter 321 rejects the unwanted elastically scattered radiation (parasitic Rayleigh signal). The SERS probe chip 310 can be attached to an external focusing lens (e.g. a ball lens) or to the semiconductor (e.g., silicon) framing the slit 116. Although not shown, the outputs of the waveguide 316 can be coupled to an optical fiber (not shown) which is coupled to a ball lens. In applications not involving Raman scattering such as high resolution absorption, reflectance, and fluorescence spectroscopy methods in the visible and infrared where there is no elastically scatter light to suppress (e.g., reflectance, absorption), the notch filter 321 can be excluded. Moreover, for applications not involving SERS, the collection chamber changes but all the compact MEMS spectrometer can remain the same.

Another monolithic spectrometer embodiment can involve pattering the optics directly on opposing sides of an optical substrate (e.g., low dispersion glass substrate), using techniques such as electron beam lithography. As with the embodiments described above, the reflective grating and the photodetector are on one side of the spectrometer, and the first and second mirrors are on the other side of the spectrometer. These would be coated with a reflective material such as protected Al or Au so that the optics operate in a reflective mode. A separate photodetector array chip in this embodiment would be bonded to a portion of the area on one side of the patterned optical substrate. This alternate embodiment advantageously decouples the spectrometer from the detector array, therefore affords the flexibility of performing high resolution spectroscopy over a wider range of wavelengths. The all reflective design of the spectrometer mitigates thermal self emission problems.

Advantages of embodiments of the invention include elimination of discrete components in favor of a rugged monolithic design, that based on appropriate material selection for the respective substrates can be a largely athermal design. This makes disclosed MEMS spectrometers generally maintenance-free from issues including component misalignment and thermal drift which are common problems that generally plague conventional optical instruments. Moreover, design approaches described above also makes the spectrometers immune to contaminants such as dust and chemical deposits that can rapidly degrade optics, and impact detection sensitivity and performance. Since the optical components and photodetector array can be bonded to be internal facing towards the optical substrate (e.g., glass), dust and other volatile vapors cannot affect them. Only the entrance slit generally needs to be kept clean to ensure that light collected from the sample enters the MEMS spectrometer. Short of breaking or cracking the part, spectrometers according to embodiments of the invention can be expected to withstand shock and vibration well (e.g., drops and bumps) and continue to function without loss in performance. These qualities make the disclosed MEMS spectrometers well adapted for field use. Embodiments of the invention are thus well adapted for diverse applications in many spectroscopy markets, including, but not limited to molecular assay developers, and chem/bio agent detection (equipment providers).

Being generally MEMS-based is another advantage provided by embodiments of the invention which provides the flexibility of generating simple static designs as well as dynamic programmable grating designs. The latter are more complicated as these gratings generally have actuators on them that can vary grating parameters including groove spacing and depth. This feature can be useful in making to device flexible for use in different applications; e.g., tuneability where the same spectrometer sensor system can be reprogrammed for different wavelength ranges and or resolution, creating nonlinearity in the dispersion, etc. for diverse applications.

EXAMPLES

Disclosed embodiments are further illustrated by the following specific Examples, which should not be construed as limiting the scope or content of this Disclosure in any way.

Some exemplary information for a prototype spectrometer based on MEMS spectrometer 100 described above is provided below. Spectrometer optical surfaces: grating ruling density of 667 line per mm, primary mirror collimating reflector (conic), and secondary mirror focusing element (8th order Asphere). Some performance parameters: inverse reciprocal dispersion (IRD) $(\Delta\lambda/\Delta s)$=200 nm/8 mm≈25 nm/mm; average blur size of ~16 micron at 85 percent encircled energy, spectral resolution≈blur size*IRD, and average spectral resolution≈0.4 nm. The MEMS spectrometer was small in size being about 60 mm×30 mm.

While various disclosed embodiments have been described above, it should be understood that they have been presented by way of example only, and not as a limitation. Numerous changes to the disclosed embodiments can be made in accordance with the Disclosure herein without departing from the spirit or scope of this Disclosure. Thus, the breadth and scope of this Disclosure should not be limited by any of the above-described embodiments. Rather, the scope of this Disclosure should be defined in accordance with the following claims and their equivalents.

Although disclosed embodiments have been illustrated and described with respect to one or more implementations, equivalent alterations and modifications will occur to others skilled in the art upon the reading and understanding of this specification and the annexed drawings. While a particular feature may have been disclosed with respect to only one of several implementations, such a feature may be combined with one or more other features of the other implementations as may be desired and advantageous for any given or particular application.

The terminology used herein is for the purpose of describing particular embodiments only and is not intended to be limiting to this Disclosure. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this Disclosure belongs. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

I claim:

1. A MEMS spectrometer, comprising:
an optical substrate having a first planar face and a second planar face parallel throughout to said first planar face;
a first semiconductor comprising substrate attached to said first planar face having a slit for passing incident light to said optical substrate, and at least one integrated reflective grating, and at least one integrated detector array, and
a second semiconductor comprising substrate attached to said second planar face, including at least a first integrated mirror and a second integrated mirror thereon,
wherein said first integrated mirror is positioned to receive said incident light transmitted by said optical substrate and provide reflected light, and said integrated reflective grating, said second integrated mirror and said integrated detector array are positioned so that they are optically coupled to one another by said optical substrate to process said reflected light.

2. The MEMS spectrometer of claim 1,
wherein said integrated reflective grating and said integrated detector array of said first substrate are both positioned on a first common side of said first substrate and said first common side is attached to face inward to said planar first face, and said first integrated mirror and said second integrated mirror are both positioned on a second common side of said second substrate and said second common side is attached to face inward to said planar second face.

3. The MEMS spectrometer of claim 1, wherein said integrated reflective grating comprises a blazed grating.

4. The MEMS spectrometer of claim 1, wherein said first semiconductor comprising substrate is attached by a first optical adhesive to said first planar face and said second semiconductor comprising substrate is attached by a second optical adhesive to said second planar face.

5. The MEMS spectrometer of claim 1, wherein said optical substrate comprises fused silica, $CaF_2$, ZnSe, sapphire, $MgF_2$ or $BaF_2$.

6. The MEMS spectrometer of claim 1, wherein said first and said second substrate comprise silicon.

7. The MEMS spectrometer of claim 1, wherein said first integrated mirror and said second integrated mirror both comprise focusing mirrors.

8. The MEMS spectrometer of claim 1, wherein said first and said second substrate comprise silicon and said integrated detector array comprises a photodiode array, an avalanche diode array or a phototransistor array.

9. A sensing system, comprising:
a probe including a light source and sample collection area that receives light from said light source for sensing a presence of at least one target when received in said sample collection area, said sample collection area emitting a detection signal responsive to said receiving said light, and
a MEMS spectrometer for receiving and processing said detection signal, wherein said MEMS spectrometer comprises:
an optical substrate having a first planar face and a second planar face parallel throughout to said first planar face;
a first semiconductor comprising substrate attached to said first planar face having a slit for passing said detection signal to said optical substrate, at least one integrated reflective grating, and at least one integrated detector array formed, and
a second semiconductor comprising substrate attached to said second planar face including at least a first integrated mirror and a second integrated mirror,
wherein said first integrated mirror is positioned to receive said detection signal transmitted by said optical substrate and provide a reflected detection signal, and said integrated reflective grating, said second integrated mirror and said integrated detector array are positioned so that they are optically coupled to one another by said optical substrate to process said reflected detection signal.

10. The sensing system of claim 9, wherein said integrated reflective grating and said integrated detector array of said first substrate are both positioned on a first common side of said first substrate and said first common side is attached to face inward to said first planar face, and said first integrated mirror and said second integrated mirror are both positioned on a second common side of said second substrate and said second common side is attached to face inward to said second planar face.

11. The sensing system of claim 9, wherein said integrated reflective grating comprises a blazed grating.

12. The sensing system of claim 9, wherein said first semiconductor comprising substrate is attached by a first optical adhesive to said first planar face and said second semiconductor comprising substrate is attached by a second optical adhesive to said second planar face.

13. The sensing system of claim 9, wherein said optical substrate comprises fused silica, $CaF_2$, $ZnSe$, $Al_2O_3$, $MgF_2$ or $BaF_2$.

14. The sensing system of claim 9, wherein said first and said second substrate comprise silicon.

15. The sensing system of claim 9, wherein said first integrated mirror and said second integrated mirror comprise focusing mirrors.

16. The sensing system of claim 9, wherein said first and said second substrate comprise silicon and said integrated detector array comprises a photodiode array, an avalanche diode array or a phototransistor array.

17. The sensing system of claim 9, wherein said probe comprises a SERS probe chip comprising a SERS substrate.

\* \* \* \* \*

UNITED STATES PATENT AND TRADEMARK OFFICE
Certificate

Patent No. 8,390,806 B1            Patented: March 5, 2013

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Suresh Subramanian, Ocoee, FL (US); and Gary C. Vanstone, Merritt Island, FL (US).

Signed and Sealed this Twenty-seventh Day of May 2014.

GREGORY J. TOATLEY, JR.
*Supervisory Patent Examiner*
Art Unit 2877
Technology Center 2800